United States Patent [19]
Tonouchi et al.

[11] Patent Number: 6,127,174
[45] Date of Patent: Oct. 3, 2000

[54] PLASMID DERIVED FROM GLUCONOBACTER BACTERIA AND VECTOR

[75] Inventors: Naoto Tonouchi; Masakazu Sugiyama; Kenzo Yokozeki, all of Kawasaki, Japan

[73] Assignee: Ajinomoto Co., Inc., Tokyo, Japan

[21] Appl. No.: 09/371,008

[22] Filed: Aug. 10, 1999

[30] Foreign Application Priority Data

Aug. 11, 1998 [JP] Japan .................................. 10-227437

[51] Int. Cl.[7] ........................... C12N 15/70; C12N 15/74
[52] U.S. Cl. ........................................................... 435/320.1
[58] Field of Search ........................................... 435/320.1

[56] References Cited

FOREIGN PATENT DOCUMENTS

| | | |
|---|---|---|
| 0 381 027 | 8/1990 | European Pat. Off. . |
| 0 758 679 A1 | 2/1997 | European Pat. Off. . |
| 59-162883 | 9/1984 | Japan . |
| WO 95/23220 | 8/1995 | Japan . |

OTHER PUBLICATIONS

Flkaya et al, "Development of a Host–Vector System for Gluconobacter Suboxydans", Agric. Biol. Chem. 49(8), 2407–2411, 1985.

Flkaya et al, "Distribution and Characterization of Plasmids in Acetic Acid Bacteria", Agric. Biol. Chem. 49(5), 1349–1355, 1985.

Masuda et al, "Plasmids of Gluconobacter Bacteria", Hakkokogaku vol. 61, No. 1, 15–18, 1983.

Primary Examiner—Terry McKelvey
Attorney, Agent, or Firm—Oblon, Spivak, McClelland, Maier & Neustadt, P.C.

[57] ABSTRACT

A shuttle vector autonomously replicable in bacteria belonging to the genera Gluconobacter and Escherichia is constructed from an endogenous plasmid of Gluconobacter oxydans IFO3171 strain, which has a size of about 5.6 kb, or a part thereof, and a plasmid autonomously replicable in bacteria belonging to the genus Escherichia or a part thereof. The present invention provides a novel plasmid useful for gene manipulation of Gluconobacter bacteria, and a shuttle vector utilizing the plasmid.

21 Claims, 2 Drawing Sheets

SEQUENCE LISTING

```
<160> NUMBER OF SEQ ID NOS: 1

<210> SEQ ID NO 1
<211> LENGTH: 5648
<212> TYPE: DNA
<213> ORGANISM: Gluconobacter oxydans

<400> SEQUENCE: 1
aagctttgca cagatccttg gtctacacgg ctcgtggaac ctcaaaggcc gcactgtagc      60
cagccaagtg aaagggaggc tcgtctaatg gggacgtttt atgaagagct ggcaaagctc     120
caacatgccc gtttcatcgg aaaaacactg gatgaggtag taaggatcga aaagatttct     180
gctaaccatc caaccaccat cgcaaggcag gccacaaagg cagaagaaca gcaaaccgtc     240
gctgatctgg acaaggcgat ggccgcgcac gttcactcaa aaatgcatcc gggtgaaaac     300
gagaagcagg catttatccg cctcgtaaac gagcatgatc ctgatgtgtc agcactctac     360
agcagacgaa aagcagctat cgcattagcc gacaaaacaa cgggtcgata atggcgcaag     420
cgtacacgcc caagggatca agaagagcct ttcagacatt catgacgctc aacaagctga     480
aatcgtcaaa gcgtctatga ccggagagac cataagcgaa aacgaaccat ggttcgagcc     540
atacaaagct catccagaaa tctacttagc tattcgaaca gcacggataa tgaggcaaaa     600
cgggatggat ggagaatgac tgtgaaaatc cgcactcaag aggacgtggc aaagcagctc     660
atccagattt acagcgatgc acgagaaggc agaattacac ccaaggccgc cgatcggctc     720
tcacgggttc tgcatcgtct caaacctctg ctccctctga atgacttcgt cgctgattta     780
gcccaattcg gaaactgaaa tggccagacc acggattacc gttgatgaag aagcccttga     840
gcatctgatc ggtcttggcg tctcaatcgg tctggcagcc gacattatgg aagtgagcga     900
aagcacgatt gcacggcacc tgaagcgcaa tccagaagct cacaaacgga tgacggcggc     960
gagaacacgg gctcagaaca cgactgattg cggaaatggt aaggcgtggg ctcaaaagca    1020
gcgacagact gctcctggca tctgtagaac gattggccgg gctcaaatct catgctcttg    1080
aaatcagcgg tccgaatggt ggtcctatcg ggcttcacca taacgctgac gtcagctcgg    1140
aaattatgac agaagccagc gagctactga aacaaatcca agaagcagct cgtaatcggg    1200
atggagatcc aagctctacc gaagtagaat aagtcttctc ctgtttccaa cgataggaag    1260
cgcgtcggtt catcccgacg cgtttctat ttctggacca tcaacacagc caaggcgcat    1320
caaagatgcg ggctacgccg ctcccgcgct gcgctcgccc ttggcatgac gggtccgtgc    1380
aaacccgttt gggtatctgc tcaagggcca atgagtggac gggaaggcca ttcctcacat    1440
ctgaagagta gagctgcgag aaatcccgta tgcctttctg caatacgcca cgagcgtgat    1500
ggtcaagatc cttggggaga ttgtagcagg ttttctcacg ttcatatctg tccagataga    1560
tgccctgaaa tttgagggca tcttctccaa cgccaccgca tctttgcgtt cgcatcgcgc    1620
```

-continued

```
cagtgaacga actcaaaatt gagggcgtca gtcgcttgca agcagacgcc ctagaataaa    1680
acagccaatc gatggtcgct tggttaagtt ttaggagaac gatcatggt aaaaacccag     1740 acgatcagaa gatgccagac ccctacttct ttttgttgtt gctaatcttt gatgtggtga    1800
tggtcagtgc tgacctgatc ggactagcgc gtctctgctg ataaaaatca gaagctgaag    1860
atgacctgca cttccttaat ggaggttcag gtcatcacca agcgcggaaa ggcgatgcgg    1920
gaattcccgc atcggtcagt aagcccaccc attaagactt catttttcctt ccaaaccata   1980 aggcaagaaa tatcatagaa gcagtaacga tttgctcgat ggtactgaga taatagcctg    2040
acaaaacggc ctcctaaaat gaaggatggc cgcctcttgt cttgcatcgg ctcgaaagat    2100
gcacttacaa cccaagaacg tcatatggtt ctccccattt atgactggcg gccgattatg    2160
gacaatcggt ccaattcaag ggctcgggtg ttacagcact cgagccctta caaatgcatt    2220
tccacatcag aagcgcactc tgcaagcgaa ctcttagctt gcaaaaagca acgagctgtg    2280
aattttgaaa tttagaacaa atctctgagt acttatccac acccgaaaaa ccaattttac    2340
ccatagacaa cggtaagtac tgaagcagtt agcctttta ggaagaaaga ataccctcaa     2400
aaaataatca cgaaacttga cgctaaattg gtcaatatta gagggtcagg taccagaaaa    2460
cattcaatca ggcggtgaac gctgcataat ccgctcccag atcaaacgat aaacgtcaca    2520
ccactcaatc ccctcggtta tcgccaactt tttagtgatg cgaatgatcc aggcatgatc    2580
gaaaacagga tgattggcag cccgcttcca aacagcaacc ggaagaagcc caacaggctt    2640
ttcgtcctgc gcttcaagct ccggctcttg ctcgtctgca atgtcttcga agtccagatc    2700
taagatcccc ttcaatcggg gaccaaccac aagcagacgt tgacctgaca gggcagaaac    2760
tgcttcggcg tacttctggc cagcaagtcg gtcaccttca gcggccaacg caagcaactc    2820
aggaacattc aggcgattag ggcgcttccc ggttttcttc catccggccg ccatctcaga    2880
agccattccc caactgcgaa gatctgcgac cccataatca gacaagcctt tgtcttcaga    2940
taccggaaca accttctgcc ctgatccaac ggcgatatga ccagccttgg ccaacaggtc    3000
gatccagcga cctgtgagcg actggcccgc actaacggcc gcctttgcgc cgtcccggtg    3060
aataacaatc gcatggacat gcagatgcca gcccgtccta cgcccccaag tcacctcaaa    3120
gacccggata aagccgacca gaccgtccct gagcagccgg ttccacaagc caccacgctg    3180
catcgcggaa atagccttag tctgaaccgt ccgcatgttt gacaggcgag tgtttcggtc    3240
atgccgcata gtccatgtgg cgaatgcagc gccgtatcca ttggcatgaa ccgctttgag    3300
gaccgcacca acccgggcag acacatcaga tgcccgtaga ggcgcacagt gagggcaacg    3360
agcagagccg caatgcgtga cgccatccac ggccaaccgc gttgatccat cccgagcagc    3420
aacagggcgg agagaaatgt gggcagtatc tttgccaggc aaaccacaag cgcggatcga    3480
acatctcacg tcatgatcgt gcaagacctt cctagaagcc ttggataacc gccatttttg    3540
ctcgtctttt gcctctgggg gggtaaaccg atttcctctg ttatcaaggg gctcagattt    3600
ggtgtccgga gctttacccg acagagcatc caaaccggca aaatcctgcc ctgacgcttt    3660
cgaagtaatc cgagcattct tggaagcgct cgacgcagaa aaatgacgtg catttggccc    3720
cttgcgggat acctcatgca gatttttat ctttccacat tgaggatttt cgggctgaaa     3780
accgctattt tttaggggtt ctttaagcaa aatccccgcc aaacatggcg gtctggtgtt    3840
gaaatcgcgc ttcaattcct gatatggaaa aagcgcggat cggggtatgc gaaaacatag    3900
cctgttctaa gttctgggcc tatttcgggc tttcgccaag ttgcaaaccg agatcagccc    3960
```

-continued

```
tgatccgtgc caccagacct aacgtagctt ctcaccggta ggcaagccct ccgacaatc    4020 tctggtattc caaaccagtg aagcgcgtct ctgcatgacc ttcttctcat cgtccctaat    4080
gatgaaaatg cctttcccgt cttagggtct gcgccagctt gcaccgacca acccaaactt    4140
aggttcgttc atcacaaagg aaatcaacgt cacatctcga acgtaataga ctgcctatcc    4200
taggtatttt cctgctctct aacgatcact cgccctgatc gtgtccgaaa gagccttttgg   4260 tctgatcatt tgtctgaccg cgcttcacgt cctgcgctac acgattgacc aactggaacg    4320
cagttttctg cacatgatca ggaacagtca gaccggcaga ggccatccgc actacaagat    4380
caactgcttg agtggcgtcg gtaagactga cagggcttac ttgtctgaca gcgacctttt    4440
tacccgcgtt cctgtctgcc ttgatcttct cgcggatggc agaggcgatc cattctccaa    4500
caccaacacc agcagtcttg gcatgtgaga cagcagcttg cttcacgtct gaaggaactc    4560
cccggatgct ccaaggtgtt gcgtcagtct gatttccggt tcatgtcata ctcctatcag    4620
cttctgtagt caggaaaagc caaagtgtct gccccacaag ggatacgtct aacaaacaga    4680
cggaaatgta gacaagagcg tcaatctgaa tgactgccac agggcttatg gcggggatgc    4740
atcaaagcgc cctggcattt agatggcgca caaggagacc aaagcgcttg tgatcgagtt    4800
ggagcctcgg gaaattcccc taccaccctt aacagaagct ctgatcaggt tttgctcggg    4860
aaaaaagacg tagggacaag acaccgtcaa aaccattttg tgcgggtttt ctcatacgct    4920
ctgaagaaac aaagagaatt ttcgcatgtc tttggaaaga cgcgattaat aatccagata    4980
caaacaaata atgcaaaaat gttctaaaat ataagaacaa ttctagtctt ctgaaatttc    5040
accaaattga agttcataga tcaaaaactt tgatatctat ctaattaaac aatagaatat    5100
ggctattatc atcacacatg gatctgatca tgacctatgg cggcactcat gccaatgcca    5160
gtcagcgcac cgggaccgaa gcgtgatctt gccgacgcga tcactcaacg ggacacactc    5220 acaaacggc tgaaagctct tcggaccaac attcaggcat gccgtggtgc aggccgagat    5280
atcccggcca atctggcatt cgatcttctg caaaccgagc gttctgtcga agccaaggaa    5340
aaagaactgg caggtctgga agtcatctgc cgggatcatc tcaagcaacg atccgaagaa    5400
gaactgaagc agaaagagaa ggctgagatt gctcaccggg aaaccgtagc agcgtactca    5460
actgaagtcc tgacggctgc caagcagact gatgacgctc tttcggcttt gatcacggcc    5520
ttcacctcat tgaagactgc aagccagagc ctaagcctac acaacggcat cacgatcgat    5580
ggatgggcta acaacccgga aagctggctc atggaagcca tgggcaccat gaacacatca    5640
gacggaaa                                                             5648
```

PLASMID DERIVED FROM GLUCONOBACTER BACTERIA AND VECTOR

BACKGROUND OF THE INVENTION

1. Field of the Invention

The present invention relates to a plasmid autonomously replicable in a bacterium belonging to the genus Gluconobacter, which is an endogenous plasmid pAG5 of *Gluconobacter oxydans* IFO3171 strain and has a size of about 5.6 kb, and a shuttle vector which is constructed from the plasmid and a plasmid derived from a bacterium belonging to the genus Escherichia. The shuttle vector is useful for gene manipulation in a bacterium belonging to the genus Gluconobacter.

2. Description of the Related Art

Bacteria belonging to the genus Gluconobacter are industrially useful microorganisms. For example, they produce D-xylulose, xylitol and the like from D-arabitol. Gene manipulation techniques are one of the effective means for breeding of further superior strains from these bacteria. In order to perform such gene manipulation of Gluconobacter bacteria, it is necessary to first develop a host-vector system for an objective bacterium. Further, on the other hand, it will be very convenient if a plasmid vector which is replicable not only in Gluconobacter bacteria but also in other host cells such as those of *Escherichia coli* (such a vector will be referred to as "shuttle vector" hereinafter) can be obtained, when gene manipulation is performed in Gluconobacter bacteria.

Plasmids derived from Gluconobacter bacteria and vectors utilizing them have so far been reported in *Hakkokogaku Kaishi*, Vol. 61, pp.15–18, (1983), Japanese Patent Unexamined Publication [KOKAI] No. 59-162883, European Patent Publication EP 0381027, International Patent Publication WO95/23220 and the like. In particular, in *Hakkokogaku Kaishi*, Vol. 61, pp.15–18 (1983), it has been reported that *Gluconobacter oxydans* IFO3171 strain harbors one kind of large plasmid (about 26 mega daltons).

BRIEF SUMMARY OF THE INVENTION

The object of the present invention is to provide a novel plasmid useful for gene manipulation of Gluconobacter bacteria and a shuttle vector utilizing such a plasmid.

The present inventors conducted studies in order to achieve the aforementioned object. As a result, they found that *Gluconobacter oxydans* IFO3171 strain harbors a novel endogenous plasmid, and thus they have accomplished the present invention.

That is, the present invention provides;

(1) a plasmid autonomously replicable in a bacterium belonging to the genus Gluconobacter, which is an endogenous plasmid of *Gluconobacter oxydans* IFO3171 strain and has a size of about 5.6 kb or a derivative thereof;

(2) the plasmid of the above item (1) which has a nucleotide sequence shown in SEQ ID NO: 1;

(3) a shuttle vector autonomously replicable in a bacterium belonging to the genus Gluconobacter and a bacterium belonging to the genus Escherichia, which is constructed from a plasmid of the above item (1) or (2) or a part thereof and a plasmid autonomously replicable in a bacterium belonging to the genus Escherichia or a part thereof;

(4) the shuttle vector of the above item (3) wherein the plasmid autonomously replicable in a bacterium belonging to the genus Escherichia is pUC18; and (5) the shuttle vector of the above item (4) which is pSG8 or pSG6.

According to the present invention, there are provided a novel plasmid derived from Gluconobacter bacteria, and a shuttle vector utilizing the plasmid. The shuttle vector can autonomously replicate in cells of Gluconobacter bacteria and *Escherichia* coli, and therefore it is useful for gene manipulation of vector DNA, and gene transfer into Gluconobacter bacteria.

DETAILED DESCRIPTION OF THE INVENTION

Hereinafter, the present invention will be explained in detail.

The novel plasmid of the present invention can be prepared from *Gluconobacter oxydans* IFO3171 strain. The IFO3171 strain can be obtained by any one from the Institute for Fermentation, Osaka (Postal code: 532-8686, 17-85, Juso-honmachi, 2-chome, Yodogawa-ku, Osaka, Japan).

The plasmid of the present invention can be obtained by culturing the IFO3171 strain in a medium such as YPG medium, and preparing a DNA fraction of cytoplasm from the obtained cells by a usual method for preparing a plasmid DNA from cells, for example, the alkali lysis method (*Nucleic Acids Res.*, 7, 1513 (1979)). Further, the DNA fraction may be purified by EtBr-CsCl equilibrium density-gradient centrifugation method, agarose gel electrophoresis and the like.

Figure 1:
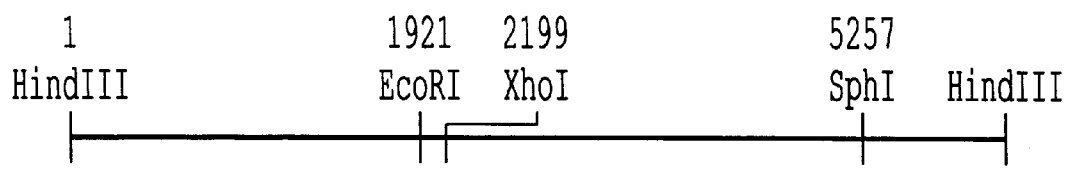
FIG. 1 shows the restriction map of the plasmid pAG5. The relative positions of several restriction sites are indicated by nucleotide number.

The plasmid of the present invention obtained in the examples described hereinafter in such a manner as mentioned above had a size of about 5.6 kb, and designated as pAG5. The pAG5 is a novel plasmid which distinctly differs in its size from the plasmid derived from the Gluconobacter oxydans IFO3171 strain (about 26 mega daltons) reported in *Hakkokogaku Kaishi*, Vol. 61, pp.15–18 (1983). The restriction map of pAG5 is shown in FIG. 1, and its nucleotide sequence is shown in SEQ ID NO: 1 of Sequence Listing. The nucleotide sequence shown in SEQ ID NO: 1 is represented from the restriction enzyme HindIII recognition site of pAG5 at the 5' end.

The plasmid of the present invention include, in addition to one having the nucleotide sequence shown in SEQ ID NO: 1, a derivative thereof autonomously replicable in Gluconobacter bacteria. Such a derivative may be one corresponding to pAG5 of which portion other than the region responsible for the replication is removed therefrom, or one corresponding to pAG5 of which part is inserted with another DNA sequence.

By ligating pAG5 to a plasmid autonomously replicable in bacterium other than Gluconobacter bacteria, a shuttle vector autonomously replicable in such bacteria can be obtained. As the bacteria other than Gluconobacter bacteria, a bacterium belonging to the genus Escherichia, specifically, *Escherichia coli*, and the like can be mentioned.

For the construction of the shuttle vector, the whole pAG5 or a part thereof may be used. When a part thereof is used, such a part must contain the region responsible for the replication of pAG5, but a region unnecessary for the replication may be excluded. The region required for the replication can be determined by ligating a part obtained by digesting pAG5 with a restriction enzyme to a plasmid autonomously replicable in *Escherichia coli*, transforming *Gluconobacter oxydans* with the obtained recombinant plasmid, and determining if the recombinant plasmid is harbored by the transformant. As an example of the partial fragment of pAG5 that has such a region, there may be exemplified a longer fragment between the two fragments obtained by digesting pAG5 with HindIII and EcoRI.

The plasmid autonomously replicable in *Escherichia coli* is not particularly limited, and examples thereof include plasmid vectors usually used for the gene manipulation utilizing *Escherichia coli*. Specifically, there can be mentioned pUC18, pUC19, pBR322, pHSG299, pHSG298, pHSG399, pHSG398, RSF1010, pMW119, pMW118, pMW219, pMW218 and the like. As also for these plasmids, whole plasmid or a part thereof may be used. When a part thereof is used, such a part must contain the region concerning the replication of pAG5, but a region unnecessary for the replication may be excluded. As for many of the usually used vectors for *Escherichia coli*, the regions required for the replication or unnecessary regions have been well known.

The shuttle vector of the present invention preferably contains a marker gene such as a drug resistance gene. As such a drug resistance gene, an ampicillin resistance gene, chloramphenicol resistance gene and the like can be mentioned. These drug resistance genes are contained in the usually used vectors for *Escherichia coli*, and they can be used as they are for the construction of the shuttle vector together with the region required for the replication. For example, pUC18 has an ampicillin resistance gene.

Further, the shuttle vector of the present invention desirably has a cloning site, preferably a multi-cloning site. Many of the plasmid vectors for *Escherichia coli* mentioned above have a multi-cloning site, and they can be used as they are for the shuttle vector of the present invention.

As examples of the shuttle vector of the present invention, pSG8 and pSG6 can be mentioned. pSG8 can be obtained by ligating pAG5 digested with restriction enzyme HindIII, and pUC18 digested with the same restriction enzyme HindIII. pSG6 can be obtained by ligating a longer fragment between the fragments obtained by digesting pAG5 with HindIII and EcoRI, and a longer fragment between the fragments obtained by digesting pUC18 with HindIII and EcoRI. These shuttle vectors are autonomously replicable in bacteria belonging to the genera Escherichia and Gluconobacter. Therefore, for example, manipulation such as insertion of a DNA fragment into the shuttle vector can be perfomed by using Escherichia bacteria, and introduction of a target gene into the Gluconobacter bacteria and the like can be performed by transforming the Gluconobacter bacteria with the obtained recombinant vector. As a cloning site, SacI, BamHI, XbaI, SalI, and PstI sites can used in pSG8, and EcoRI and HindIII sites can used in pSG6.

When Gluconobacter bacteria are transformed by using the shuttle vector of the present invention, a usual transformation method, for example, the electric pulse method and the like can be used. The Gluconobacter bacteria may be preferably exemplified by *Gluconobacter oxydans*.

BEST MODE FOR CARRYING OUT THE INVENTION

Hereinafter, the present invention will be explained further specifically with reference to the following examples.
(1) Isolation and purification of plasmid

*Gluconobacter oxydans* IFO3171 strain was cultured in YPG medium (Yeast Extract 0.5%, Bacto-Peptone 0.3%, glucose 3%, pH 6.5), and cells were harvested by centrifugation. From these cells, a cytoplasmic DNA fraction was extracted by a usual alkali lysis method (*Nucleic Acids Res.*, 7, 1513 (1979)), and separated and purified by agarose gel electrophoresis. As a result, a novel plasmid of about 5.6 kb was found, and designated as pAG5.

A restriction map prepared based on digestion of pAG5 with several restriction enzymes is shown in FIG. 1.
(2) Determination of nucleotide sequence The nucleotide sequence of pAG5 was determined by the dideoxy termination method. The sequencing reaction was performed by using Dye Terminator Cycle Sequencing Kit (produced by ABI) according to the instruction attached to the kit. The electrophoresis was performed by using DNA Sequencer 373 (produced by ABI). The determined nucleotide sequence is shown in SEQ ID NO: 1 in Sequence Listing.
(3) Construction of shuttle vector pAG5 was digested with restriction enzyme HindIII. The digestion product and the vector plasmid pUC18 of *Escherichia coli* (containing ampicillin resistance gene) which was digested by HindIII were mixed, and ligated by DNA ligase. By using the ligation product, *Escherichia coli* JM109 strain was transformed by the competent cell method. A strain harboring the chimeric plasmid of pAG5 and pUC18 (about 8.3 kb) was selected from the transformants which exhibited ampicillin resistance, and the chimeric plasmid was designated as pSG8.

Figure 2:
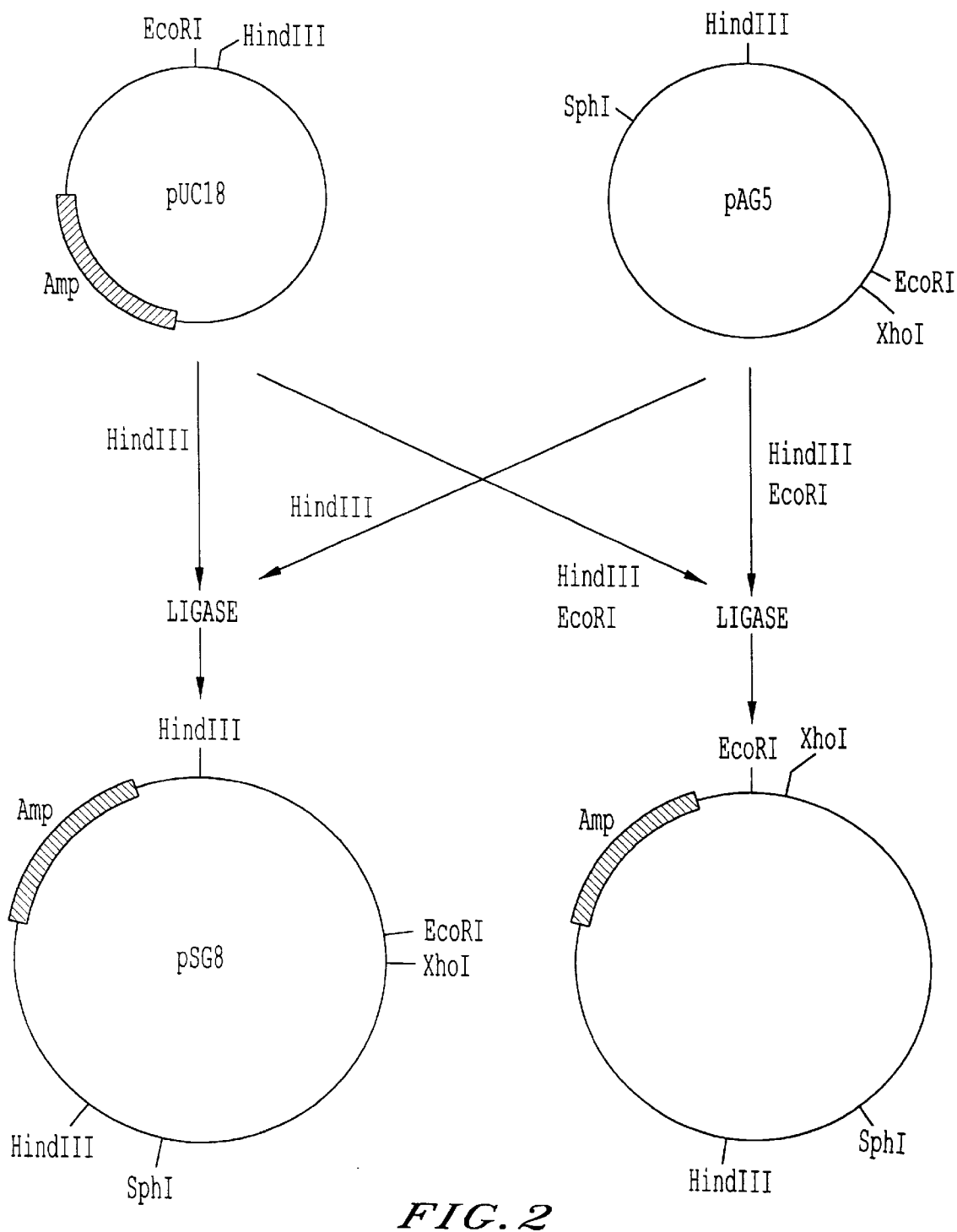
FIG. 2 shows the outline of the construction of the shuttle vectors pSG8 and pSG6.

Further, pAG5 was digested with restriction enzymes HindIII and EcoRI. The digestion product and the vector plasmid pUC18 of *Escherichia coli* which was digested with HindIII and EcoRI were mixed, and ligated by DNA ligase. By using the ligation product, *Escherichia coli* JM109 strain was transformed by the competent cell method. A strain harboring the chimeric plasmid of a part of pAG5 and pUC18 (about 6.4 kb) was selected from the transformants which exhibited ampicillin resistance, and the chimeric plasmid was designated as pSG6. The outline of the construction of pSG8 and pSG6 is shown in FIG. 2.

The *Escherichia coli* JM109 strain harboring pSG8 was given a private number of AJ13485, and it was deposited in the Patent Microorganism Depository, National Institute of Bioscience and Human-Technology, Agency of Industrial Science and Technology, Ministry of International Trade and Industry (poatal code 305-8566, 1-3 Higashi 1-chome, Tsukuba-shi, Ibaraki-ken, Japan) on Jul. 21, 1998, and assigned an accession number of FERM P-16903, and transferred from the original deposit to the international deposit based on Budapest Treaty on Jun. 14, 1999, and has been deposited as an accession number of FERM BP-6760.

(4) Transformation of *Gluconobacter oxydans* ATCC621 strain using chimeric plasmids The *Gluconobacter oxydans* ATCC621 strain was cultured in YPG medium. The cells harvested by centrifugation were washed with 10% sucrose solution, resuspended in 10% sucrose solution, and mixed with the chimeric plasmid pSG8 or pSG6 (100 μg/ml). The transformation was performed by the electric pulse method by applying an electric pulse of 1400 V for 7 times using a cell fusion apparatus Shimadzu SSH-10 (produced by Shimadzu). An ampicillin resistant strain was obtained in the both cases using the plasmids pSG8 and pSG6. The plasmids were separated from these strains by the alkali lysis method, and analyzed by agarose gel electrophoresis. As a result, it was confirmed that the trans formants harbored the introduced plasmids.

What is claimed is:

1. An isolated plasmid autonomously replicable in a bacterium belonging to the genus Gluconobacter which is the endogenous plasmid of *Gluconobacter oxydans* IFO3171 strain and has a size of about 5.6 kb.

2. The isolated plasmid of claim 1, which has the nucleotide sequence of SEQ ID NO: 1.

3. The isolated plasmid of claim 1, which is autonomously replicable in a bacterium belonging to the genus Gluconobacter and a bacterium belonging to the genus Escherichia.

4. The isolated plasmid of claim 1, which further comprises a marker gene.

5. The isolated plasmid of claim 4, wherein the marker gene is a drug resistance gene.

6. The isolated plasmid of claim 1, which further comprises a multiple cloning site, wherein said multiple cloning site comprises a restriction site for at least one restriction enzyme selected from the group consisting of EcoRI, HindIII, SacI, BamHI, XbaI, SalI and PstI.

7. A plasmid comprising a *Gluconobacter oxydans* replication region which is obtained by digesting the endogenous plasmid of claim 1 with one or more restriction enzymes to obtain a fragment of the endogenous plasmid, licating the fragment to a plasmid autonomously replicable in *Escherichia coil* to obtain a chimeric plasmid, transforming a *Gluconobacter oxydans* cell with the chimeric plasmid, and determining if the chimeric plasmid is harbored by the transformant, wherein if the chimeric plasmid is harbored by the transformant, it is a plasmid comprising a *Gluconobacter oxydans* replication region.

8. The plasmid comprising a *Gluconobacter oxydans* replication region of claim 7, which is autonomously replicable in a bacterium belonging to the genus Gluconobacter and a bacterium belonging to the genus Escherichia.

9. The plasmid comprising a *Gluconobacter oxydans* replication region of claim 7, wherein said fragment is responsible for autonomous replication in a bacterium belonging to the genus Gluconobacter.

10. The plasmid comprising a *Gluconobacter oxydans* replication region of claim 7, wherein said restriction enzyme is selected from the group consisting of HindIII, EcoRI, XhoI and SphI.

11. The plasmid comprising a *Gluconobacter oxydans* replication region of claim 7, which further comprises a marker gene.

12. The plasmid of claim 11, wherein the marker gene is a drug resistance gene.

13. The plasmid of claim 12, which is pSG8 or pSG6.

14. The plasmid comprising a *Gluconobacter oxydans* replication region of claim 7, which further comprises a multiple cloning site, wherein said multiple cloning site comprises a restriction site for at least one restriction enzyme selected from the group consisting of EcoRI, HindIII, SacI, BamHI, XbaI, SalI and PstI.

15. An isolated plasmid comprising at least one restriction enzyme fragment of SEQ ID NO: 1.

16. The plasmid of claim 15, which is autonomously replicable in a bacterium belonging to the genus Gluconobacter and a bacterium belonging to the genus Escherichia.

17. The plasmid of claim 15, wherein said restriction enzyme fragment is responsible for autonomous replication in a bacterium belonging to the genus Gluconobacter.

18. The plasmid of claim 15, wherein said restriction enzyme fragment is generated by digestion of SEQ ID NO: 1 with at least one enzyme selected from the group consisting of HindIII, EcoRI, XhoI and SphI.

19. The plasmid of claim 15, which further comprises a marker gene.

20. The plasmid of claim 19, wherein the marker gene is a drug resistance gene.

21. The plasmid of claim 15, wherein the plasmid further comprises a multiple cloning site, wherein said multiple cloning site comprises a restriction site for at least one restriction enzyme selected from the group consisting of EcoRI, HindIII, SacI, BamHI, XbaI, SalI and PstI.

* * * * *